United States Patent [19]

Shibe, Jr. et al.

[11] 4,096,089
[45] Jun. 20, 1978

[54] SALT OF SULFONATED STYRENE OLIGOMER, METHOD OF PREPARATION THEREOF, AND USE THEREOF AS DISPERSING AGENT AND VISCOSITY REDUCER

[75] Inventors: William J. Shibe, Jr.; William Wood, both of Moorestown, N.J.

[73] Assignee: Sybron Corporation, Rochester, N.Y.

[21] Appl. No.: 775,564

[22] Filed: Mar. 8, 1977

[51] Int. Cl.$^2$ .................. B01J 13/00; C07C 143/24
[52] U.S. Cl. .............................. 252/310; 106/308 S; 252/313 R; 252/353; 260/505 N; 260/505 R
[58] Field of Search .............................. 252/310, 353; 106/308 S; 260/505 N, 505 R

[56] References Cited

U.S. PATENT DOCUMENTS

| | | | |
|---|---|---|---|
| 2,097,726 | 11/1937 | Grotowsky | 260/505 R X |
| 3,126,293 | 3/1964 | McSheehy et al. | 106/308 S X |
| 3,179,613 | 4/1965 | Guenther et al. | 260/505 R X |

FOREIGN PATENT DOCUMENTS

| | | | |
|---|---|---|---|
| 773,488 | 4/1957 | United Kingdom | 260/505 N |
| 920,898 | 3/1963 | United Kingdom | 260/505 R |

*Primary Examiner*—Richard D. Lovering
*Attorney, Agent, or Firm*—Theodore B. Roessel; Papan Devnani

[57] ABSTRACT

A method of effectively utilizing styrene still bottoms waste material is described. The waste material is primarily styrene oligomer which is sulfonated and used as a dispersing agent.

5 Claims, No Drawings

SALT OF SULFONATED STYRENE OLIGOMER, METHOD OF PREPARATION THEREOF, AND USE THEREOF AS DISPERSING AGENT AND VISCOSITY REDUCER

BACKGROUND OF THE INVENTION

In the manufacturing process of styrene monomer, to obtain purity, the styrene monomer is distilled. During this distillation step, the thermal reaction causes the formation of styrene oligomer which remains as residue in the still bottoms. The oligomer is a heavy oily viscous liquid and is differentiated from polymer as having an average molecular weight of less than $10^3$ (300–750 or 3–8 styrene units). About 2.5% of total styrene monomer distilled forms oligomer, and yearly approximately 150,000,000 lbs are produced. The disposal of these oligomers has produced a serious environmental problem. EPA regulations forbid manufacturers from discharging the bottoms into effluent water streams. Some manufacturers have tried to burn it as a fuel which is highly undesirable as due to its high aromatic content these bottoms produce smoke and peculiarly offensive odor.

It is therefore an object of this invention to provide a method of effectively utilizing these styrene bottoms waste material.

It is another object of this invention to provide a dispersing agent produced from styrene bottoms.

It is yet another object of this invention to provide a salt of sulfonated styrene oligomer.

The foregoing objects and others are accomplished in accordance with this invention by providing a dispersing agent made out of styrene bottoms by sulfonating them and subsequently forming an alkaline salt of it. The advantages of this method will become apparent upon consideration of the following disclosure of the invention.

The dispersing agent of the present invention is prepared as follows:

Styrene still bottoms can be sulfonated either by chlorosulfonic acid or by sulfur trioxide. The sulfonated oligomers are dark brown in color and completely soluble in sodium, potassium, and ammonium hydroxide. Sodium salts of the sulfonated styrene oligomer were prepared as follows:

EXAMPLE I

Sulfur trioxide of Styrene Still Bottoms Using Sulfurtrioxide

Equipment:
 1-liter three-necked flask
 mechanical agitator
 2-500 ml. addition funnels
 Claissen head
 2 Thermometers 0°–150° C.
 Distillation Head
 Condenser
 Water Bath
 Heating mantle

| Raw Materials: | |
|---|---|
| Styrene still bottoms | 102g. |
| Dry Ethylene dichloride | 400g. |
| SO$_3$ | 85g |
| Sodium hydroxide | 47g. |
| Cetyl alcohol | 1–2g. |
| Triethyl phosphate | 10g. |

Procedure
 Step 1. Add 220 grams of dry ethylene dichloride to flask.
 2. Add 10 grams of triethyl phosphate.
 3. Turn on agitator and cool to 15° C.
 4. Place 85 grams of SO$_3$ (1.06M) in one addition funnel.
 5. Place a mixture of 200 ml of dry ethylene dichloride and 104 grams of styrene still bottoms in second addition funnel.
 6. Add approximately 5–6g. SO$_3$ from addition funnel to reaction flask.
 7. Add concurrently the contents of two addition funnels to reaction flask keeping temperature below 20° C. 60–70 minutes addition time.
 8. Allow mass in reaction flask to agitate 1 hour.
 9. Add to reaction flask 40 grams of sodium hydroxide in 340 grams of water (10.5%). Keep temperature below 40° C.
 10. Agitate 1 hour.
 11. Turn off agitator and allow two phases to separate.
 12. Remove lower phase (ethylene dichloride) (365–375g).
 13. Replace Claissen head and addition funnel distillation head and condenser, with thermometers for pot temperature and head temperature.
 14. Distill off dissolved ethylene dichloride. Some foaming may occur. Can be controlled by adding 1–2 grams Cetyl alcohol.
 15. Adjust water phase to a value of pH 7 with 20% sodium hydroxide (30–40 ml.).

Yield
 510–520 grams 40% solids of sulfonated styrene still bottoms.
 370–395 grams of wet ethylene dichloride recovered containing 1.25–1.50% water insoluble solids (94–98%).
 % yield on SO$_3$ 98+%
 % yield on styrene 96–98%

EXAMPLE II

Sulfonation of Styrene Still Bottoms using Chlorosulfonic Acid 104 (1M) gms. styrene still bottoms was dissolved in 400g of ethylene dichloride and charged into 1-liter three-neck flask. 8g. of Potassium diacid phosphate was added to flask. With rapid agitation 127g. (1.1M) chlorosulfonic acid was added dropwise (15–30) minutes. The mass in flask was warmed to 40° C. and agitated until HCl evolution ceases (3 hrs). 80g. of NaOH dissolved in 300 ml. water was added cautiously. Agitated for 1 hour and allowed phases to separate. Yield 603.7 grams of 38.1% sulfonated styrene still bottoms. 366.5 grams of ethylene dichloride recovered.

Alkaline salts of sulfonated styrene oligomers such as sodium salts, potassium, ammonium and amine salts are completely soluble, and calcium, zinc, and aluminum salts are partly soluble.

The following reaction took place to form the sodium salts of styrene oligomer sulfonate.

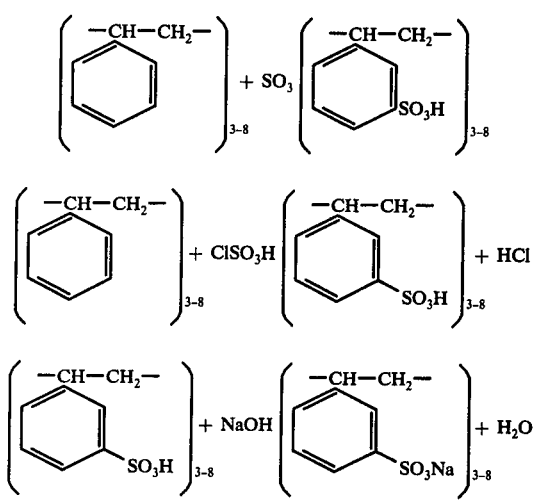

The sodium salt of styrene oligomer sulfonate is used as an effective dispersing agent. Its properties were compared with other dispersants widely used by the industry such as TAMOL N (Reg. Trademark of Rohm & Haas) and LOMAR (Reg. Trademark Nopco division of Diamond Shamrock Corp) which are sodium salts of a condensed arylsulfonic acid. Physical properties of sulfonated styrene oligomer dispersant as compared to TAMOL N are as follows. The surface tension and interfacial tension (U.S.P. mineral oil/water) containing the dispersant is shown below:

|  | Surface tension | | |
| --- | --- | --- | --- |
|  | 1% in sol. | 5% in sol. | pH of 1% sol. |
| Sulfonated Styrene Oligomer Dispersant | 55 dynes | 52 dynes | 9.0 |
| TAMOL N (Reg. TM) | 58 | 43 | 9.3 |

Finely divided small particles of solids when stirred into a liquid medium tend generally to agglomerate into clumps and settle out. Addition of dispersing agents overcomes this tendency in the preparation of inks, paints, cosmetic, ointments and salves. Following example were made in the laboratory to demonstrate the utility of sulfonated styrene oligomer dispersant.

EXAMPLE III

Two Polyethylene jars A and B were taken and were filled with the following:

|  | Jar A | Jar B |
| --- | --- | --- |
| Clean Steel Shot | 175 gms | 175 gms |
| Demineralized Water | 78 | 78 |
| Milori Blue pigment | 20 | 20 |
| 10% aqueous solution of Tamol N (Reg. TM) | 2 | — |
| 10% aqueous solution of sulfonated styrene oligomer | — | 2 |

Both the jars were given two 15 minute cycles on the Red Devil Paint Shaker and were evaluated visually for change in viscosity and for dispersability using a NPIRI (National Printing Ink Research Institute) Grind Gauge. After the first 15 minute cycle the Jar B showed a greater viscosity than Jar A and the dispersability on the grind gauge also indicated that Jar B having sulfonated styrene oligomer dispersant had better dispersability. After the second 15 minute cycle, the viscosity of both samples had increased with sulfonated styrene oligomer still having a higher viscosity but the dispersability on the grind gauge gave similar results. The test shows that identical doses of sulfonated styrene oligomer dispersant gave a higher rate of dispersability than that obtained with TAMOL N.

Spray dried sulfonated styrene oligomer dispersant was dissolved in various solvents and its solubility was determined as follows:

| Dispersant gm/100 ml Solvent | |
| --- | --- |
| Cellosolve | 1.6 |
| Heptane | 0.0 |
| Toluene | 0.2 |
| Methanol | 2.0 |
| Kerosene | 0.02 |
| Ethanol | 0.35 |
| Carbon Tetrachloride | 0.02 |
| Water | completely |

This data shows that the dispersant is compatible with water and polyhydroxy products and not with aliphatic, aromatic solvents or chlorinated aliphatic solvents.

The dispersant of this invention could also be used to reduce the viscosity of water dispersions. To illustrate this effect, stiff pastes or moist masses were made with pigments which are difficult to wet. These pastes normally require the presence of relatively large amounts of water to flow. The addition of small amounts of sulfonated styrene bottoms oligomer converted the pastes to free-flowing liquids. The reduction in viscosity permits the production of dispersion of higher solids content and thus promotes more efficient use of grinding and milling equipment. The dispersant of this invention has excellent property of improving flowability of pigments.

EXAMPLE IV 50 gms of pigment was wetted with enough water to form a stiff, slightly moist mass. This mass was titrated with 3.5% aqueous solution of sulfonated styrene oligomer dispersant solution until the mass became fluid and would flow. The following results were obtained.

| Pigment | ml $H_2O$ to moisten | ml of Dispersant to flow |
| --- | --- | --- |
| Aluminum silicate (clay) | 14 ml | 1 ml |
| Titanium dioxide | 17 ml | 12 ml |

The alkaline salt of sulfonated styrene oligomer could be used as wetting agent for solids such as carbon black, clays and pigments. It could also be used as a milling, grinding and mixing aid without frothing and foaming. Further it could be used as a flowing aid for pumping of high solid clay and pigmented dispersions.

Though the above examples were carried out with the sodium salt of sulfonated styrene oligomer, potassium and ammonium salts will give the same results and therefore they are not described in detail here.

Thus, it should be appreciated that the present invention accomplishes its intended objects in providing a method of effectively utilzing styrene bottoms waste material which is used as an effective dispersing agent. Though the preparation and use of alkaline salts of sulfonated styrene oligomer described here, other salts of sulfonated styrene oligomer are possible and are encompassed within this disclosure. Although specific components proportions and procedures have been stated in the above description of the preferred embodiments of the novel compound and methods, other suitable materials and procedures may be employed to synergize, enhance or otherwise modify the novel compound and methods. Other modifications and ramifications of the present invention would appear to those skilled in the art upon a reading of this disclosure. These are intended to be included within the scope of this invention.

I claim:

1. A compound having the formula

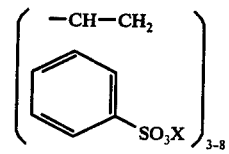

where X is Na, K, or ammonium.

2. A method of obtaining compound of claim 1 comprising forming an aromatic sulfonate of styrene still oligomer and subsequently forming a salt.

3. The method of claim 2 wherein the salt is an alkaline salt.

4. A method of dispersing a solid in water comprising adding the compound of claim 1 to said water containing said solid.

5. A method of reducing viscosity of a water dispersion comprising adding thereto an aqueous solution of the compound of claim 1.

* * * * *